United States Patent [19]

Birks et al.

[11] Patent Number: 4,806,485
[45] Date of Patent: Feb. 21, 1989

[54] METHOD OF IMPROVING THE DETECTION LIMITS OF UV-VIS ABSORBING COMPOUNDS IN HPLC BY THE USE OF A SINGLET OXYGEN TRAP

[75] Inventors: John W. Birks; Curtis L. Shellum, both of Boulder, Colo.

[73] Assignee: Cooperative Institute for Research in Environmental Sciences Univers. of Colorado, Boulder, Colo.

[21] Appl. No.: 19,880

[22] Filed: Feb. 27, 1987

[51] Int. Cl.[4] .................................................. G01N 30/14
[52] U.S. Cl. ..................................... 436/140; 422/70; 73/61.1 C; 436/161; 210/656
[58] Field of Search ..................... 436/139, 140, 161; 422/70; 73/61.1 C; 210/656, 749

[56] References Cited

PUBLICATIONS

Uihlein, M; Schwab, E., Chromatographia, 1982, 15, 140.
Birks, J. W.; Frei R. W., Trends in Anal. Chem., 1982, 1, No. 15, 361.
Kawaoka, K.; Khan, A. U.; Kearns, D. R., J. Chem. Phys., 1967, 46, 1842.
Weinberger, R.; Yarmchuk, P.; Cline Love, L. J., Anal. Chem. 1982, 54, 1557.
Donkerbroek, J. J.; van Eikema Hommes, N.J.R.; Gooijer, C.; Velthorst, N. H.; Frei, R. W., Chromatographia, 1982, 55, 1886.
Donkerbroek, J. J.; Veltkamp, A. C.; Gooijer, C.; Velthorst, N. H.; Frei, R. W., Anal. Chem. 1983, 55, 1886.
Gollnick, K.; Franken, T.; Schade, G.: Dorhofer, New York Acad. Sci., 1970, 171, 89.
Young, R. H.; Wehrly, K.; Martin, R. L., J. Amer. Chem. Soc., 1971, 93, 5774.
Poulsen, J. R.; Birks, J. W.; Guibitz, G.; van Zoonen P.; Gooijer, C.; Velthorst, N. H.; Frei, R. W., J. Chromatogr., 1986, 360, 371.
Krinski, N. I. in Singlet Oxygen, Organic Chemistry, A Series of Monographs, H. H. Wasserman and R. W. Murry, eds, vol. 40, Academic Press, N.Y., p. 602, 1979.
Yound, R. H.; Chinh, N.; Mallon, C., Ann New York Acad. Sci., 1970, 171, 130.
Kasha, M., J. Opt. Soc. Am., 1948, 38, 929.
Birks, J. W., Gandelman, M. S., Brinkman, U. A., Frei, R. A.; J. Chromatagr., 1983, 282, 193.
Gandelman, M. A., Birks, J. W.; Anal. Chim. Acta, 1983, 155, 159.

Primary Examiner—Barry S. Richman
Assistant Examiner—Timothy M. McMahon
Attorney, Agent, or Firm—Morgan & Finnegan

[57] ABSTRACT

A post-column photochemical reaction method to improve the detection limits of compounds which absorb radiation in the range of 240 nm to 800 nm has been developed for high performance liquid chromatography (HPLC). Specifically, the limit of detection of HPLC has been reduced to a range of from about 0.5 pg to about 10 pg for a large class of organic compounds which promotes the formation of "singlet oxygen". These compounds transfer excitation energy to ground state oxygen, forming the excited singlet species, $O_2$ ($^1\Delta g$). Singlet oxygens in turn react with a substituted furan such as 2,5-dimethylfuran (DMF) or 2,5-diphenylfuran (DPF). UV absorption or fluorescence is used to detect either the loss of the substituted furan or the appearance of the oxidation product of the substituted furan. The reaction is photocatalytic in nature and results in a large chemical amplication of the signal. Detection limits are improved by one to two orders of magnitude for a wide variety of UV-absorbing compounds.

20 Claims, 6 Drawing Sheets

METHOD OF IMPROVING THE DETECTION LIMITS OF UV-VIS ABSORBING COMPOUNDS IN HPLC BY THE USE OF A SINGLET OXYGEN TRAP

INTRODUCTION

The present invention relates to a method for improving the detection limits of organic compounds in high performance liquid chromatography (HPLC) by the use of a post column photochemical reaction involving the production of singlet oxygen and the oxidative reaction thereof with substituted furans. More specifically, the post column photochemical reaction is one wherein the molecules of the analyte are promoted to an excited triplet state by the absorbance of radiation at a wavelength greater than about 240 nm. The energy of the excited molecules is then transferred to oxygen dissolved in the mobile phase to produce singlet oxygen, which then oxidizes the substituted furans and like compounds added to the mobile phase. The substituted furan and like compounds may be oxidized to produce an ultraviolet (UV) or visible (VIS) light absorbing or fluorescent product, or the UV/VIS absorbing or fluorescent substituted furan may be oxidized to form a less absorbing or less fluorescent product. The increase in absorbance of the product or the decrease in UV/VIS absorbance or fluorescence of the reactant may be monitored, and the signal is an indication of the amount of the analyte injected.

BACKGROUND OF THE INVENTION

High performance liquid chromatography (HPLC) has become one of the most useful analytical tools in a modern chemical laboratory. It is particularly useful for the room temperature separation and analysis of very small amounts of organic or biochemical compounds. Most commonly, in HPLC a spectrophotometer is used to detect the presence of the analyte, since most organic compounds will absorb radiation in the range of about 190 nm to 800 nm, particularly in the UV range of about 190 nm to 350 nm.

Although HPLC is a powerful analytical tool for the separation and detection of low amounts of organic or biochemical compounds, sufficiently low detection limits are still not currently available for many analytes including conjugated aromatic and non-aromatic compounds, such as polycyclic aromatic compounds, including substituted naphthalenes and anthracenes; anthraquinones; biphenyls, polychlorinated biphenyls; aromatic and non-aromatic nitrogen, oxygen and sulfur containing heterocyclic compounds, conjugated non-aromatic compounds such as biacetal and its derivatives where very low detection limits are desired. For example, the process of this invention is particularly suitable for the detection of very low amounts of pharmaceuticals in body fluids or toxic substances in the environment.

Phosphorescence or fluorescence has been considered to improve the sensitivity of the detection limit of HPLC (1). However, many UV or VIS absorbing compounds have low or negligible fluorescence quantum yields (2), or only phosphoresce at low temperatures or in organized media.

A photochemical method of transforming UV absorbing compounds such as Clobazam and Fenbendazole into fluorescent substances has been reported (1). However, this approach requires the analyte compound to be transformable to fluorescent compounds, and few organic compounds meet this requirement. Other photochemical methods using a post-column photochemical reactor to enhance detection limits have also been reported (3,13,14). These include a colorimetric method of determining nitroso compounds by photohydrolysis to nitrites; photolytic decomposition of halogen, or nitrogen or sulfur containing compounds; and the photoreduction of anthraquinone derivatives by glycosides and saccharides. However, these methods are generally applicable only to very specific types of compounds.

Several approaches to the use of phosphorescence in HPLC have been suggested including micelle stabilized room temperature phosphorescence (4), sensitized room temperature phosphorescence (5) and phosphorescence quenching (6). However, all of these approaches require the careful removal of virtually all dissolved oxygen from the solvents which are used for dissolving the samples containing the analyte(s) and the mobile phase. This necessity of rigorous oxygen removal is a severe disadvantage. Furthermore, none of these approaches have resulted in substantial improvements in the detection limits when compared to conventional UV absorption.

Many efforts have been made to study the photochemical reaction of organic compounds in the presence of oxygen (2, 7, 8, 9, 10, 11, 14). The research efforts indicate that molecular oxygen reversibly quenches the excited singlet and triplet states of many organic molecules, i.e. fluorescent or phosphorescent organic molecules.

It is also known that the interaction of molecular oxygen with electronically excited molecules lead to the formation of a metastable excited singlet state oxygen (3). Metastable singlet oxygen apparently is the responsible intermediate in certain photooxygenation reactions of two classes of organic compounds: (A) those that have the structural element of cis-1,3-dienes and those that are polycyclic aromatic compounds and heterocyclic compounds such as furans; or (B) olefins containing allylic hydrogen atoms (7).

Compounds which are electronically excitable, i.e. compounds which absorb radiation at a wavelength greater than 240 nm to produce triplet state molecules with a quantum yield greater than about 0.05, with a triplet state lifetime greater than about $10^{-6}$ seconds, and have triplet state energies above 22.5 kcal/mole have been found to be useful to catalyze the photooxygenation reaction.

It has been reported that xanthene dyes and rose bengal when excited by light energy can transfer the energy to oxygen molecules to form singlet oxygen which then reacts with 1,3-diphenylisobenzofuran or 2,5-dimethylfuran (7) and (8). Many other organic compounds have been shown to be good sensitizers for singlet oxygen formation (7).

A solid-state peroxyoxalate chemiluminescence detection of hydrogen peroxide generated in a post column reaction using HPLC has been reported recently (8). Hydrogen peroxide was generated in a post column photochemical reaction from the analyte quinone separated and eluted by HPLC. The amount of hydrogen peroxide was detected using solid state peroxyoxalate energy transfer chemiluminescence of bis-2,4,6-trichlorophenyl oxalate. However, using this method the detection limits of quinone derivatives have not been found to be improved from that of using UV absorption.

Post column photochemical reactors have also been described (1, 2, 9, 13, 14). Uihlein and Schwab described the use of a post column photochemical reaction chamber made from polytetrafluoroethylene (PTFE) tubing. The chamber is made by knitting thin PTFE tubing with 0.5 mm I.D. into a strand of loops which were then supported around a light source by being woven on a star shaped device. The knitted reaction chamber, without the use of a column, showed band broadening of HETP of 1.9 cm (1).

A reaction chamber knitted into a cylinder from thin PTFE tubing to fit around a fluorescent lamp tube and a pyrex tube was also described (13,14). The use of a crocheted post column chemical reactor was mentioned by Poulsen and Birks et al. (9).

None of these developments have led to a method for improving the detection limits of HPLC by the use of the photocatalyzed reactions of substituted furans, bilirubin, chlorophylls, substituted pyrroles, substituted imidazoles, and substituted olefins.

The object of the present invention is to develop a method of improving the detection limits of HPLC for a class of radiation absorbing organic compounds without the need of rigorous removal of oxygen dissolved in the solvents.

A second object is to improve the detectability of most radiation absorbing organic compounds in HPLC by at least an order of magnitude.

A further object is to improve the detectability of most radiation absorbing organic compounds in HPLC by a simple and convenient post column photochemical reaction.

REFERENCES

1. Uihlelin, M; Schwab, E., *Chromatographia*, 1982, 15, 140.
2. Birks, J. W.; Frei R. W. *Trends in Anal. Chem.*, 1982, 1, No. 15, 361.
3. Kawaoka, K.; Khan, A. U.; Kearns, D. R., *J. Chem. Phys.*, 1967, 46, 1842.
4. Weinberger, R.; Yarmchuk, P.; Cline Love, L. J., *Anal. Chem.* 1982, 54, 1557.
5. Donkerbroek, J. J.; van Eikema Hommes, N. J. R.; Gooijer, C.; Velthorst, N. H.; Frei, R. W., *Chromatographia*, 1982, 55, 1886.
6. Donkerbroek, J. J.; Veltkamp, A. C.; Gooijer, C.; Velthorst, N. H.; Frei, R. W., *Anal. Chem.* 1983, 55, 1886.
7. Gollnick, K.; Franken, T.; Schade, G.; Dorhofer, *Ann. New York Acad. Sci.*, 1970, 171, 89.
8. Young, R. H.; Wehrly, K.; Martin, R. L., *J. Amer. Chem. Soc.*, 1971, 93, 5774.
9. Poulsen, J. R.; Birks, J. W.; Gubitz, G.; van Zoonen, P.; Gooijer, C.; Velthorst, N. H.; Frei, R. W., *J. Chromatogr.*, 1986, 360, 371.
10. Krinski, N. I. in *Singlet Oxygen, Organic Chemistry, A Series of Monographs*, H. H. Wasserman and R. W. Murry, eds., Vol. 40, Academic Press, New York, p. 602, 1979.
11. Young, R. H.; Chinh, N.; Mallon, C., *Ann New York Acad. Sci.*, 1970, 171, 130.
12. Kasha, M., *J. Opt. Soc. Am.*, 1948, 38, 929.
13. Birks, J. W., Gandelman, M. S., Brinkman, U. A., Frei, R. A.; *J. Chromatagr.*, 1983, 282, 193.
14. Gandelman, M. S., Birks, J. W.; *Anal. Chim. Acta*, 1983, 155, 159.

BRIEF DESCRIPTION OF THE INVENTION

The present invention relates to a method of improving the detectability in high performance liquid chromatography of aromatic organic compounds comprising:

A. Modifying a conventional HPLC apparatus having an injection port, an analytical column and a spectrophotometric detector by inserting between the analytical column and the spectrophotometric detector, a photochemical reactor comprising:
  (i) at least one lamp which emits radiation in the range of from about 190 nm to 800 nm;
  (ii) a photochemical reaction chamber having two open ends, with one open end connected to the analytic column and the other open end connected to the spectrophotometer; and
  (iii) a filter device interposed between the lamp and the reaction chamber to selectively transmit a desired activation wavelength;

B. Dissolving a sample containing an analyte to be detected in a suitable solvent to form a sample solution, the analyte being selected from the group of conjugated compounds comprising aromatic and non-aromatic compounds and derivatives thereof which are excitable by radiation of a selected excitation wavelength greater than 240 nm to produce triplet state molecules with a quantum yield greater than about 0.05, having an average lifetime greater than about $10^{-6}$ seconds and a transferable excitation energy of at least about 22.5 kcal/mole;

C. Selecting a suitable mobile phase for the analyte;

D. Adding a singlet oxygen trap selected from the group consisting of substituted furans, bilirubin, chlorophylls, substituted pyrroles, substituted imidazole, and substituted olefins in the mobile phase at a concentration in the range of $10^{-5}$ to $10^{-2}$ M;

E. Injecting the sample solution via the injection port and allowing the sample solution to pass through the analytical column and the photochemical reactor; and F. Monitoring the signal generated in the spectrophotometric detector at a predetermined wavelength.

DETAILED DESCRIPTION OF THE INVENTION

Figure 1:
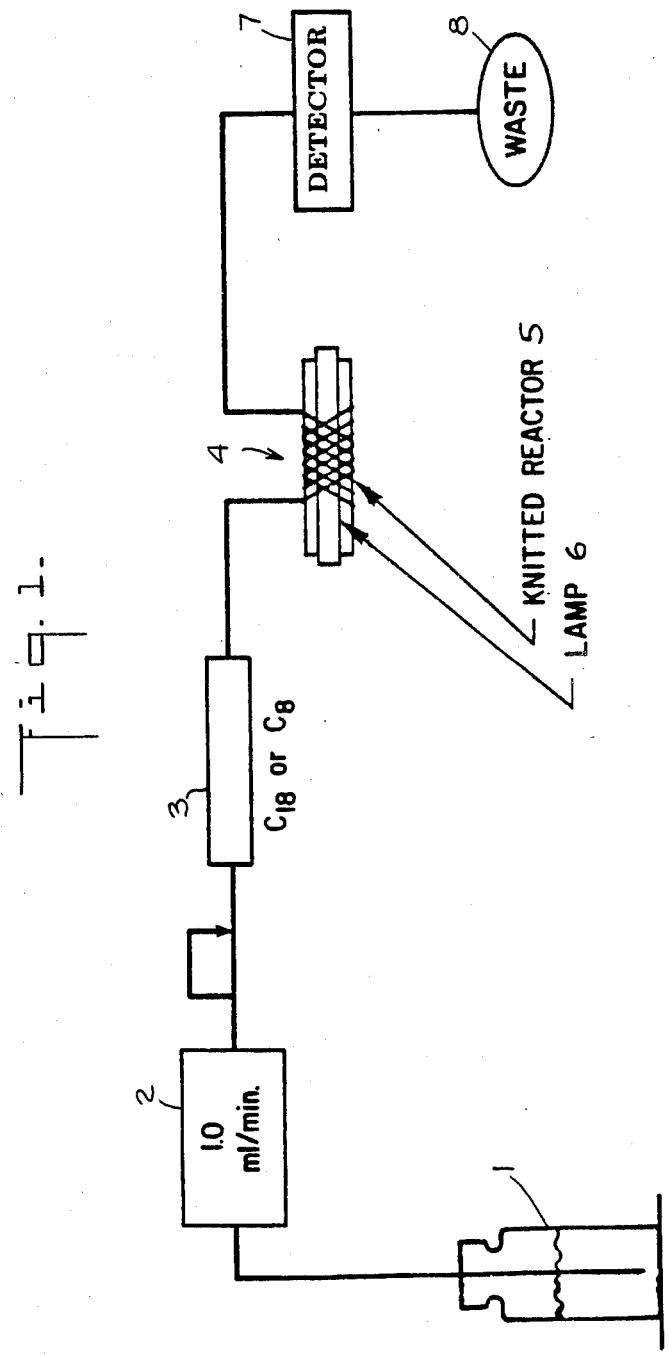
FIG. 1 is a schematic diagram of an HPLC apparatus modified with the photochemical reactor. (1) is the container for the mobile phase, (2) is the HPLC pump, (3) is the HPLC analyte column, (4) is the photochemical reactor comprising a reaction chamber (5) wrapped around a light source (6), (7) is the spectrophotometric detector and (8) is the waste receptacle.

The present invention relates to a photochemical method of enhancing the detection limit in high performance liquid chromatography (HPLC) of an analyte which absorbs radiation in the range of about 190 nm to 800 nm by the addition of a singlet oxygen reactive compound to the mobile phase for the analyte.

The method for improving the detection of an analyte by HPLC comprises:

A. Modifying a conventional HPLC apparatus having an injection port, an analytical column and a spectrophotometric detector by inserting, between the analytical column and the spectrophotometric detector, a photochemical reactor comprising:
(i) at least one lamp which emits radiation in the range of from about 190 nm to 800 nm;
(ii) a photochemical reaction chamber having two open ends, with one open end connected to the analytical column and the other open end connected to the spectrophotometric detector; and
(iii) a filter device interposed between the lamp and the reaction chamber to selectively transmit a desired activation wavelength;

B. Dissolving a sample containing an analyte to be detected in a suitable solvent to form a sample solution, the analyte being selected from the group of conjugated compounds comprising aromatic and non-aromatic compounds and derivatives thereof which are excitable by a selected activation wavelength greater than 240 nm to produce triplet state molecules with a quantum yield greather than about 0.05, having an average life time greater than about $10^{-6}$ seconds, and a transferable excitation energy of at least about 22.5 kcal/mole;

C. Selecting a suitable mobile phase for the analyte;

D. Adding a singlet oxygen trap selected from the group consisting of substituted furans, bilirubin, chlorophylls, substituted pyrroles, substituted imidazoles and substituted olefins to the mobile phase at a concentration of about $10^{-5}$ to $10^{-2}$M;

E. Injecting the sample solution via the injection port and allowing the sample solution to pass through the analytical column and the photochemical reactor; and F. Monitoring the signal generated in the spectrophotometric detector at a predetermined wavelength.

The singlet oxygen trap useful for the present invention is selected from the group consisting of substituted furans such as 2,5-dimethylfuran (DMF), 2,5-diphenylfuran (DPF), and 1,3-diphenylisobenzofuran (DPBF). Other compounds each of which may also be useful as a singlet oxygen trap include bilirubin; chlorophylls; substituted pyrroles, such as 1-phenylpyrrole, 1-methylpyrrole; substituted imidazoles, such as 2,4,5-triphenylimidazole, tetraphenylimidazole, 1,2-dimethylimidazole; and substituted olefins, such as 2,3-dimethyl-2-butene, cis-diethoxyethylene, 2,3,4-trimethyl-2-pentene. The compounds react with singlet oxygen to produce products with spectrophotometric characteristics that are different from the parent compounds. The singlet oxygen trap is generally added to the mobile phase at a concentration of about $10^{-5}$ to $10^{-2}$M.

The method uses the reaction of singlet state oxygen molecules with a variety of compounds, preferably the substituted furans, as singlet oxygen traps. The reaction products have highly different spectrophotometric responses from the singlet oxygen trap compound itself. It is the difference in spectrophotometric response that is monitored.

The analyte for which the detection limits in HPLC are enhanced or improved are those that undergo a photochemical reaction with oxygen to produce singlet oxygen. The analyte generally is a conjugated compound comprising an aromatic compound, a non-aromatic compound or a derivative thereof which absorb radiation at a wavelength greater than 240 nm to produce triplet state molecules with a quantum yield greater than about 0.05, having an average triplet state lifetime greater than $10^{-6}$ seconds and a transferable excitation energy of at least 22.5 kcal/mole. Examples of such conjugated compounds also include aromatic compounds wherein the aromatic ring is substituted with one or more electron withdrawing moieties selected from the group consisting of halides, nitrates, carboxylates, aldehydes or ketones and biacetal and derivatives of biacetal. Specific examples of such compounds include: aromatic hydrocarbons such as anthracene, naphthalene, benzo(a)pyrene, dibenz(a,c)anthracene, fluorene, perylene, and phenanthrene; substituted aromatic compounds such as 9-nitronaphthalene, 2-chloroanthracene, 9-anthracene carboxylic acid, 2-aminoanthracene, and 2-methylanthracene; biphenyl and polychlorinated biphenyls, such as 4,4'-dichlorobiphenyl, 2-chlorobiphenyl, 2,4'-dichlorobiphenyl, 2,4,2'-trichlorobiphenyl and 2,2'4,4'-tetrachlorobiphenyl; quinones such as anthraquinone, 2-methylanthraquinone, 2-tert-butylanthraquinone, and 1,5-dichloroanthraquinone; aromatic and non-aromatic nitrogen containing heterocyclic compounds such as quinolines and carbazoles; aromatic and non-aromatic sulfur containing heterocyclic compounds such as dibenzothiophene; biacetal and its derivatives such as 2,3-pentanedione, 1,2-diphenyl-1,2-ethanedione.

Various configurations for a post-column photochemical reactor can be used. Generally, the photochemical reactor comprises a light source, a wavelength filter device and a reaction chamber.

The light source emits radiation in the range of 190 nm to 800 nm. Low pressure mercury lamps, xenon arc lamps, xenon mercury lamps and quartz halogen lamps may be used as the light source. Preferably, the light source is a low pressure mercury lamp where no cooling is necessary. Most preferably, the light source is a pencilled shaped low pressure mercury lamp.

The wavelength filter device selectively transmits the desired activation wavelength. When DMF or DPF are used as the singlet oxygen trap, the desired excitation wavelength is 254 nm. When 1,3-diphenylisobenzofuran (DPBF) is used, a visible light source is preferred. When the light source is a low pressure mercury lamp, the filter device is preferably in the shape of a cylinder which surrounds the entire lamp. When 2,5-dimethylfuran is used as the singlet oxygen trap, the filter can be a quartz tube of about 2 mm in wall thickness.

The photochemical reaction chamber comprises a long narrow length of tubing, preferably arranged in a configuration to provide continuous convolutions to avoid laminar flow, with one end connected to the analyte column and the other end connected to the spectrophotometric detector of the HPLC. The tubing should be made of light transmissible material. The light transmissable material may be quartz or polytetrafluoroethylene, preferably the latter. The tubing should be of sufficient volume to provide a reaction time of about 0.5 to 3 minutes and yet with a sufficiently narrow internal diameter and fabricated into a design to avoid too much band broadening. It has been found that PTFE tubing, having an internal diameter of about 0.1 to 2 mm, knitted, crocheted or convoluted with many twists and turns, is suitable for use as the reaction chamber.

The specific details of a reaction chamber preferred for the process of the present invention is as follows. The reaction chamber is crocheted from 5 to 20 meters of PFTE tubing with an internal diameter of about 0.3 mm into a sleeve to fit around the combination lamp and filter device. Such a reaction chamber is found to have a residence time of between about 0.5 to 3 minutes when the flow rate is adjusted to be in the range of about 0.5 ml/min to 1 ml/min. One end of the PTFE tubing is connected to the analyte column with a zero dead volume Swagelok connector and the other end is connected to the spectrophotometric detector with another zero dead volume Swagelok connector.

The following is a brief discussion of the theoretical basis of the method of the present invention. The discussion presents a theory to explain how detectability is enhanced for the radiation absorbing analytes. However, it is to be understood that the invention is not to be bound by the theoretical discussion nor should it be construed to limit the scope of the invention.

The molecules of the analyte compound absorbs radiation from the light source and are promoted to an excited triplet state. The excitation energy of the triplet state molecules is transferred to oxygen molecules dissolved in the mobile phase to produce singlet oxygen molecules. The singlet oxygen molecules rapidly react with the singlet oxygen trap in the mobile phase to produce an oxidized product. The analyte molecule may absorb light many times during its residence time in the photochemical reactor and cause the oxidation of many singlet oxygen trap molecules. The photochemically amplified reaction thus produces a large change in the spectrophotometric response. For example, if the product of the photochemical reaction has a high UV absorbance at a particular wavelength compared to the singlet oxygen trap compound at the same wavelength, the UV absorbance of the product may be monitored. Alternatively, if the singlet oxygen trap is itself highly absorptive or fluorescent and the oxidized product is not, then the decrease in absorbance or fluorescence of the singlet oxygen trap may be monitored.

The present invention, therefore, requires either the use of a singlet oxygen trap which has high absorbance or fluorescence or the use of a singlet oxygen trap which forms a product which has high absorbance or fluorescence as compared with the analyte.

One problem in the use of a post column photoreaction to enhance the detectability of an analyte is the self photooxidation of the singlet oxygen trap compound. For example, when 2,5-dimethylfuran (DMF) is used in combination with a low pressure mercury lamp, self photooxidation may result from wavelengths shorter than 254 nm. For 2,5-diphenylfuran, minimum self photooxidation occurs at 254 nm. Therefore a filter, either a solution filter for DPF or a quartz filter for DMF is necessary. For 2,5-diphenyisobenzofuran (DPBF), which absorbs strongly at 254 nm, only a lamp which emits visible radiation, such as a xenon arc lamp or a quartz halogen lamp can be used. Its use is, therefore, limited to the enhancement of the detectability of colored compounds which absorb radiation in the range of about 400 nm to 800 nm.

The following examples illustrate the present invention and are not to be construed as limiting the scope thereof.

All of the experiments were conducted using the following equipment and materials.

EXPERIMENTAL SECTION

HPLC Apparatus

The chromatographic equipment comprised a Kratos Spectroflow 400 solvent pump, a Rheodyne 7125 injector (20 uL loop), a Zorbax ODS column (25 cm×4.6 mm) packed with 5-um C-18 particles, a Kratos Spectroflow 773 variable wavelength UV detector or a Kratos FS 950 fluorometric detector with a medium-pressure mercury excitation source, with a 326±11 nm band pass filter which served as the excitation filter, and an emission filter which passed wavelengths longer than 370 nm. A Shimadzu C-R3A integrating recorder was used to plot chromatograms and integrate the peaks generated.

Photochemical Reactor

The photochemical reactor consists of one or two low-pressure Hg pencil lamps separated from a crocheted PTFE reactor by either a cylinder of quartz or a quartz sleeve containing a solution of 2,7-dimethyl-3,6-diazacyclohepta-2,6-diene iodate, which serves as a 254 nm bandpass filter (11). The path length through the filter is 4 mm, and the solution concentration is 0.042 g/l. It was found that with DPF the use of the solution filter was required, while for DMF the short wavelength cutoff of commercial quartz of greater than 2 mm thickness was adequate to minimize the degree of self photooxidation induced by emission lines other than 254 nm.

The construction of the crocheted PTFE reaction chamber for the post-column photochemical reactor is as follows. PTFE tubing (Small Parts Inc., SST-30) having a 0.30 mm internal diameter was crocheted into a cylinder having a diameter slightly larger than the cylindrical filter device. The reaction chamber used in this work is made from 5 to 20 meters of PTFE tubing and provides reaction times of 0.5 to 3 minutes for flow rates in the range 0.5 to 1.0 ml/min. Crocheting the reactor tubing greatly reduces the degree of band broadening caused by this length of post-column tubing. The exterior of the reactor is wrapped with a light reflective foil, preferably an aluminum foil, to increase the photon flux.

It was found that baseline drift was substantially reduced by immersion of the exterior of the reactor in an ice bath. The ice bath did not significantly affect peak heights or the extent of self photooxidation, but reduced low-frequency noise, apparently by stabilizing the lamp temperature and thereby stabilizing the photon flux. The effect of temperature stabilization of the effluent passing through the UV absorption cell may also be important.

Reagents 2,7-dimethyl-3,6-diazacyclohepta-2,6-diene iodate was prepared as described by Kasha (11) and was recrystalized from methylene chloride. The substituted furans 2,5-dimethylfuran and 1,3-diphenylisobenzofuran was obtained from Eastman Kodak, while 2-methylfuran and 2,5-diphenylfuran were obtained from Aldrich. The solvents methanol, acetonitrile and water were HPLC grade.

EXAMPLE 1

Figure 2:
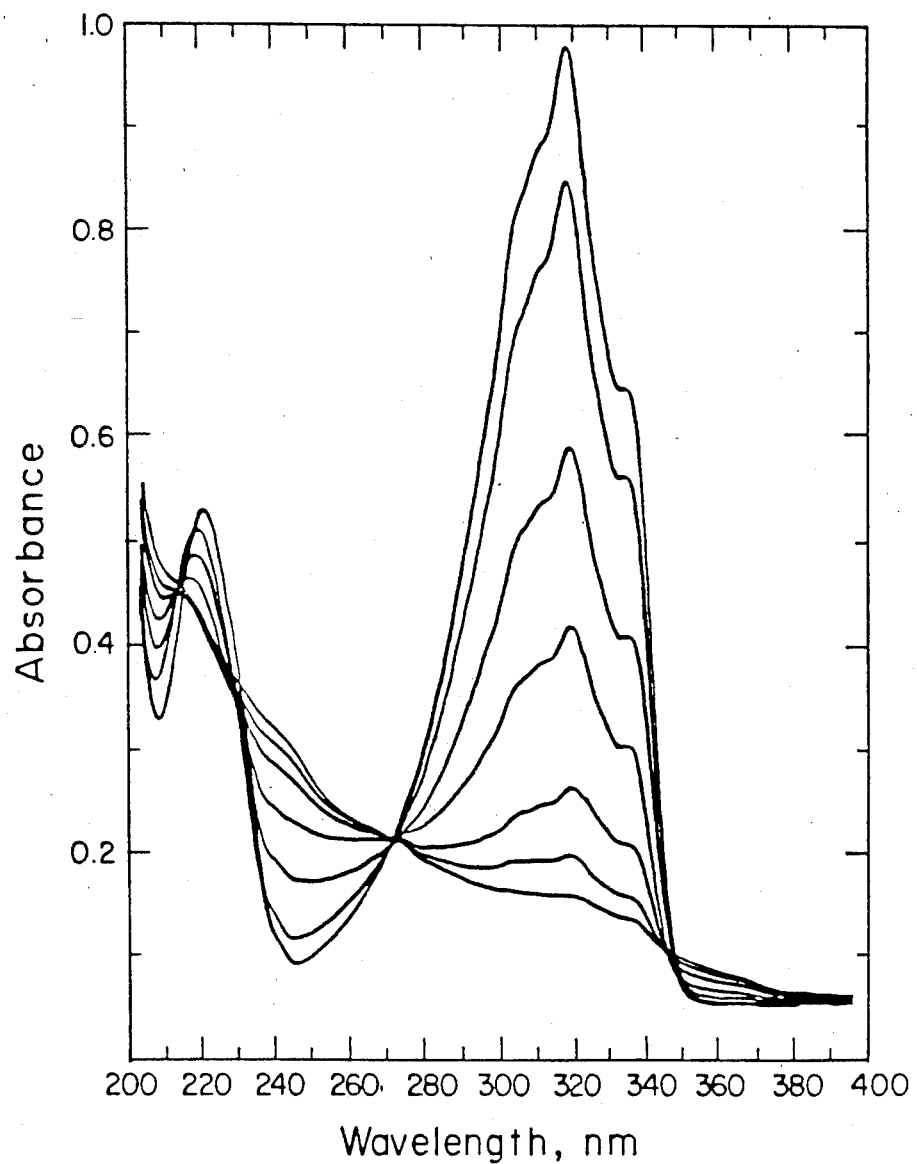
FIG. 2 shows the change in the absorption spectrum of a $3 \times 10^{-5}$ M solution of 2,5-diphenylfuran (DPF) in acetonitrile upon irradiation in a cuvette by a low pressure mercury lamp.

The change in the absorption spectrum with a time of a $3\times10^{-5}$M solution of 2,5-diphenylfuran (DPF) in acetonitrile upon irradiaion in a cuvette by a low pressure mercury lamp was recorded and is shown in FIG. 2. The decrease in UV absorption at a wavelength of 320 L nm; i.e. photobleaching, shows the decrease of DPF in the solution. Since this change in absorbance at 320 nm was the largest, it was found to give the lowest limits of detection.

To detect analytes via photobleaching of DPF, the mobile phase for HPLC was a solution of 0.5 to $1.0\times10^{-4}$M DPF in 95% acetonitrile-water by volume and the absorbance at 320 nm was monitored. The large background absorbance, in the range of 0.5 to 1.0 absorbance units (a.u.) was electronically subtracted by using the zero offset feature of the UV detector, and the leads carrying the signal to the integrating recorder were reversed so that the chromatographic peaks were positive.

Figure 3:
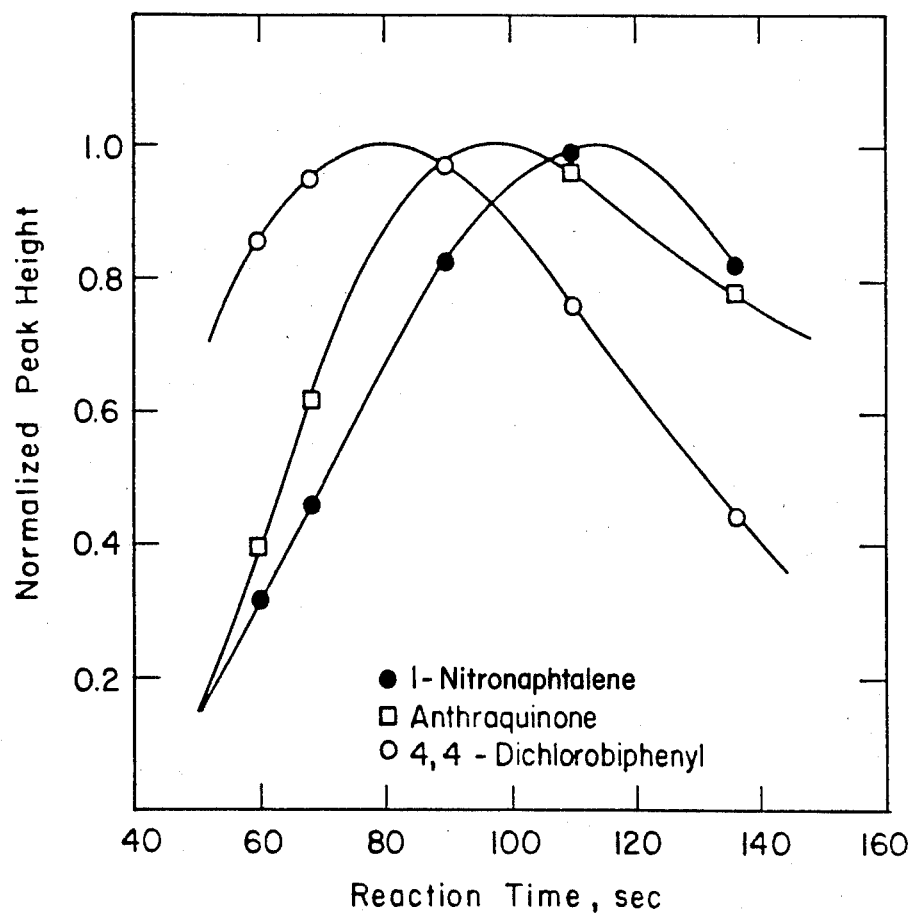
FIG. 3 shows the effect of the reaction time on the peak heights for 1-nitronaphthalene, anthraquinone and 4,4'-dichlorobiphenyl in 95% acetonitrile-water by volume containing $10^{-4}$ M DPF.
Figure 4:
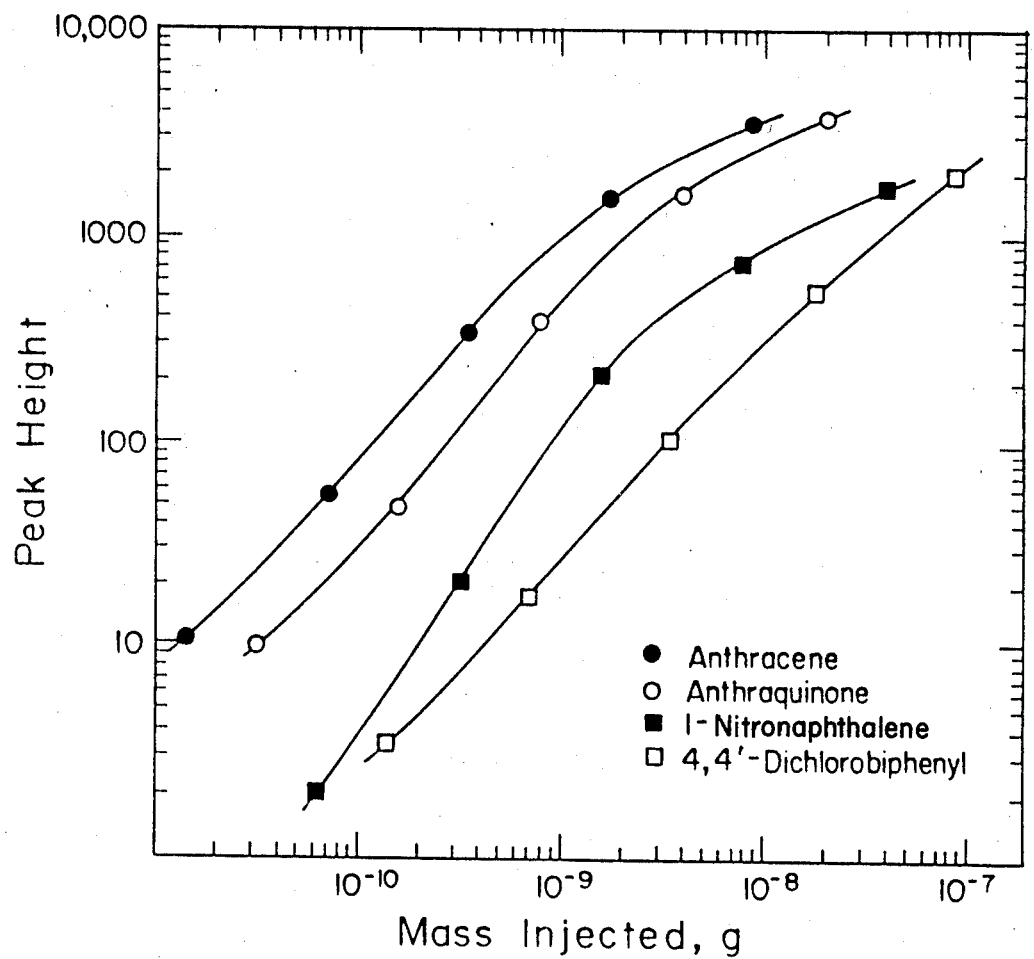
FIG. 4 shows the working curves for anthracene, anthraquinone, 1-nitronaphthalene and 4,4'-dichlorobiphenyl in the same solvent system as FIG. 3.

The effect of reaction time on peak height was determined for 1-nitronaphthalene, anthraquinone and 4,4'-dichlorobiphenyl in 95% by volume acetonitrile-water containing $10^{-4}$ DPF using two photochemical lamps. The results were plotted and are shown in FIG. 3. The optimum reaction time was found to fall in the range of 1 to 2 minutes.

The detection limits for DPF photobleaching were determined for six compounds. For these measurements the HPLC flow rate was 0.7 ml/min., the photochemical reaction time was 75 seconds using two low pressure mercury lamps, and the concentration of DPF in the mobile phase was $10^{-4}$M in 95% acetonitrite-water by volume. The exterior of the photoreactor was immersed in an ice bath to reduce baseline drift. The limits of detection are here defined as the mass of analyte injected which will produce a peak height that is $3\times$ the peak to peak noise of the baseline. The results are summarized in Table I.

TABLE I

| Compound | Detection Limit Comparisons Diphenylfuran Photobleaching | | |
|---|---|---|---|
| | Optimized UV Absorbance | Photobleaching | Enhancement Factor |
| Anthracene | 45 pg (253 nm) | 1.5 pg | 30x |
| Anthraquinone | 90 pg (250 nm) | 8.0 pg | 11x |
| 1-nitro-naphthalene | 160 pg (243 nm) | 3.6 pg | 44x |
| Quinoline | 900 pg (234 nm) | 40.0 pg | 22x |
| Biphenyl | 130 pg (260 nm) | 20.0 pg | 6.5x |
| 4,4'-dichloro-biphenyl | 90 pg (270 nm) | 10.0 pg | 9x |

The detection limits range from 1.5 pg for anthracene to 40 pg for quinoline. This was compared with the detection limits for these six compounds using direct UV absorbance at the $\lambda_{max}$ for each of the compounds using the same UV spectrophotometer. The enhancement factors were found to range from $6.5\times$ for biphenyl to $44\times$ for 1-nitronaphthalene.

EXAMPLE 2

The dependency of the detection limits on the solvent using for the mobile phase was determined by using 5%, 25% and 50% (v:v) water in acetonitrile without using an analytical column. The results based on peak area are shown in Table II.

TABLE II

| Effect of Solvent Composition on DPF Photobleaching | | | |
|---|---|---|---|
| | Relative Peak Area | | |
| Compound | 5% $H_2O$ | 25% $H_2O$ | 50% $H_2O$ |
| Anthracene | 1.0 | 0.98 | 1.6 |
| Anthraquinone | 1.0 | 0.68 | 0.71 |
| 1-nitronaphthalene | 1.0 | 1.1 | 1.3 |
| Quinoline | 1.0 | 1.1 | 1.3 |
| Biphenyl | 1.0 | 0.80 | 0.68 |
| 4,4'-dichlorobiphenyl | 1.0 | 0.70 | 1.0 |

These results indicate that a wide range of solvent conditions may be used.

EXAMPLE 3

Figure 5:
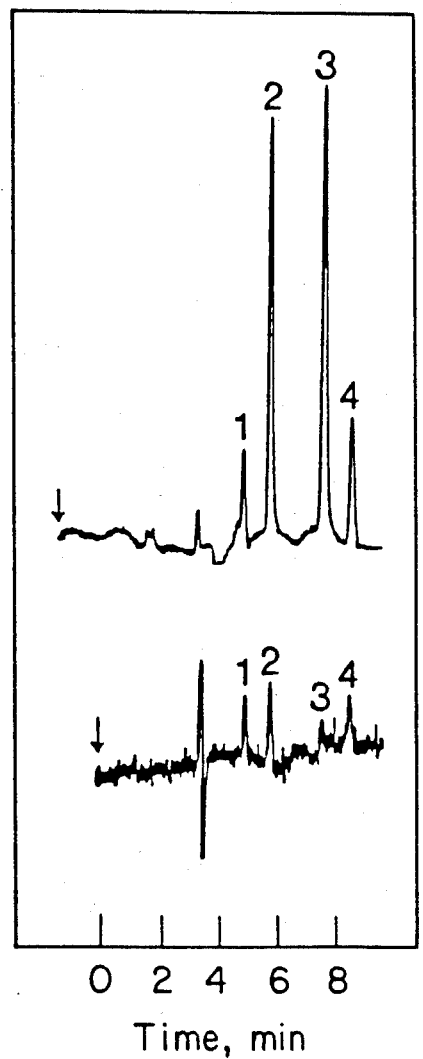
FIG. 5 shows the chromatograms of a mixture of anthracene (1), anthraquinone (2), 1-nitronaphthalene (3) and 4,4'-dichlorobiphenyl (4) in 95% acetonitrile-water by volume. The top chromatogram was obtained using the photochemical reactor with the same solvent system given in FIG. 3, and the bottom chromatogram was obtained by monitoring absorbance at 254 nm without using the photochemical reactor.

Working curves for the determination of anthracene, anthraquinone, 1-nitronaphthalene and 4,4'-dichlorobiphenyl were determined using $10^{-4}$M DPF in 95% (v:v) acetonitrile-water as the mobile phase using a postcolumn photoreactor with two low pressure mercury lamps. The working curves are shown in FIG. 5.

Figure 6:
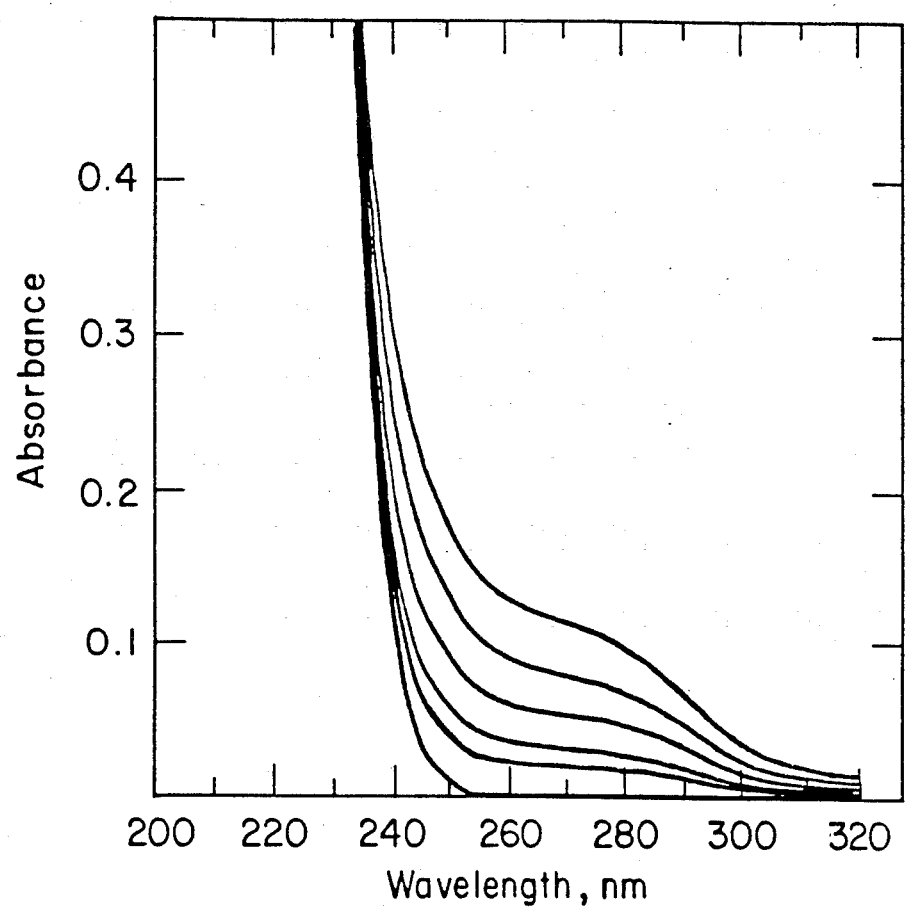
FIG. 6 shows the change in absorbance of $10^{-3}$M 2,5-dimethylfuran (DMF) in 95% acetonitrile-water by volume upon irradiation for varying lengths of time.

A chromatogram of a mixture of these four compounds was made using the post column photochemical reactor with DPF photobleaching at 320 nm. The amount of each compound was as follows: 1-nitronaphthalene, 0.32 ng; anthraquinone, 0.16 ng; anthracene, 0.072 ng; 4,4'-dichlorobiphenyl, 0.70 ng. The mobile phase was 95% acetonitrile-water by volume containing $10^{-4}$M DPF and the flow rate was 0.7 ml/min. The reaction time was 75 seconds. On the chromatogram, the order of elution is 1-nitronaphthalene, anthraquinone, anthracene and 4,4'-dichlorobiphenyl. The result is shown as the upper chromatogram in FIG. 6.

A second chromatogram of the same amount of a mixture of these four compounds were made by monitoring the absorbance at 254 nm without using the post column photochemical reactor. The result is shown as the lower chromatogram in FIG. 6. It can be observed that the improvement in detection limits is very striking.

EXAMPLE 4

A solution of $10^{-3}$M 2,5-dimethylfuran (DMF) in 95% acetonitrile-water by volume was irradiated and the change in absorbance over time was recorded in FIG. 7. An increase in absorbance at a wavelength in the range of 250 to 290 nm can be observed. Using a wavelength at 280 nm, the detective limits for six compounds were determined using $10^{-3}$M DMF first in 95% acetonitrile-water by volume and then in 95% methanol-water by volume as the mobile phase. The reaction time was 120 seconds with two lamps. The results are shown in Table III.

TABLE III

Detection Limit Comparisons
Dimethylfuran Product Absorbance

| Compound | Optimized UV Absorbance | Acetonitrile | | Methanol | |
|---|---|---|---|---|---|
| | | Absorbance at 280 nm | Enhancement Factor | Absorbance at 280 nm | Enhancement Factor |
| Anthracene | 45 pg (253 nm) | 10. pg | 4.5x | 20. pg | 2.3x |
| Anthraquinone | 90 pg (250 nm) | 1.5 pg | 60x | 5.0 pg | 1.8x |
| 1-nitronaphthalene | 160 pg (243 nm) | 10. pg | 16x | 50 pg | 3.2x |
| Quinoline | 900 pg (234 nm) | 45. pg | 20x | 300 pg | 3.0x |
| Biphenyl | 130 pg (260 nm) | 40. pg | 3.3x | 50 pg | 2.6x |
| 4,4'-dichlorobiphenyl | 90 pg (270 nm) | 20. pg | 4.5x | 60 pg | 1.5x |

The detection limits were enhanced by factors which ranged from 3.3× for biphenyl to 60× for anthraquinone.

EXAMPLE 5

The effect of the presence of water on the photochemical reaction was determined for four compounds using the conditions of Example 4. The results are presented in Table IV. These results indicate that a wide range of solvent compositions are useful in the process.

TABLE IV

Effect of Solvent Composition on DMF Product Formation

| | Relative Peak Area | | |
|---|---|---|---|
| Compound | 5% H$_2$O | 25% H$_2$O | 50% H$_2$O |
| Anthraquinone | 1.0 | 1.7 | 1.3 |
| 1-nitronaphthalene | 1.0 | 0.83 | 0.59 |
| Quinoline | 1.0 | 0.82 | 1.1 |
| Biphenyl | 1.0 | 1.7 | 1.9 |

We claim:

1. A method of improving the detection limit of aromatic compounds in HPLC comprising:
   (A) Modifying a conventional HPLC apparatus having an injection port, an analytical column and a spectrophotometric detector by inserting between the analytical column and the spectrophotometric detector a photochemical reactor comprising:
      (i) at least one lamp which emits radiation in the range of from about 190 nm to 800 nm;
      (ii) a photochemical reaction chamber having two open ends with one open end connected to the analytical column and the other end to the spectrophotometric detector; and
      (iii) a filter device interposed between the lamp and the reaction chamber to selectively transmit a desired excitation wavelength;
   (B) Dissolving a sample containing an anlyte to be detected in a solvent suitable for dissolving the analyte to form a sample solution, the analyte being selected from the group of conjugated compounds comprising aromatic compounds, non-aromatic compound and derivatives thereof which is excitable by radiation of a selected wavelength of greater than 240 nm to produce triplet state molecules with a quantum yield greater than about 0.05, with an average life time greater than 10$^{-6}$ seconds and having a transferable excitation energy of at least about 22.5 kcal/mole;
   (C) Selecting a mobile phase suitable for separating each of the compounds in the analyte and from the sample;
   (D) Adding a singlet oxygen trap selected from the group consisting of substituted furans, bilirubin, chlorophylls, substituted pyrroles, substituted imidazoles, and substituted olefins to the mobile phase at a concentration in the range of 10$^{-5}$ to 10$^{-2}$M;
   (E) Injecting the sample solution into the injection port and allowing the sample solution to pass through the analytical column and the photochemical reactor; and
   (F) Monitoring the signal generated in the spectrophotometric detector at a predetermined wavelength thereby detecting aromatic compounds contained in the sample.

2. A method according to claim 1 wherein the singlet oxygen trap is 10$^{-3}$M 2,5-dimethylfuran in 95% acetonitrile-water by volume.

3. A method according to claim 1 wherein the mobile phase is acetonitrile, methanol or mixtures of acetonitrile or methanol with water.

4. A method according to claim 1 wherein the signal monitored is UV absorbance.

5. A method according to claim 1 wherein the singlet oxygen trap is about 10$^{-5}$ to 10$^{-2}$M 2,5-diphenylfuran in 95% acetonitrile-water by volume.

6. A method according to claim 5 wherein the signal monitored is the photobleaching of 2,5-diphenylfuran at 320 nm.

7. A method according to claim 1 wherein the analyte is selected from the group consisting of anthracene, 1-nitornaphthalene, anthraquinone, quinoline, biphenyl, and 4,4'-dichlorobiphenyl.

8. A method according to claim 7 wherein the singlet oxygen trap is 10$^{-3}$M 2,5-dimethylfuran in 95% acetonitrile-water by volume.

9. A method according to claim 7 wherein the singlet oxygen trap is about 10$^{-5}$ to 10$^{-2}$M 2,5-diphenylfuran in 95% acetonitrile-water by volume.

10. A method according to claim 9 wherein the signal monitored is the photobleaching of 2,5-diphenylfuran at 320 nm.

11. A method according to claim 1, wherein the analyte is selected form the group consisting of polyaromatic hydrocarbons, aromatic compounds substituted with electron withdrawing groups, quinones, nitrogen-containing heterocyclic compounds and sulfur-containing heterocyclic compounds.

12. A method according to claim 11 wherein the singlet oxygen trap is 10$^{-3}$M 2,5-dimethylfuran in 95% acetonitrile-water by volume.

13. A method according to claim 11 wherein the singlet oxygen trap is about 10$^{-5}$ to 10$^{-2}$M 2,5-diphenylfuran in 95% acetonitrile-water by volume.

14. A method according to claim 13 wherein the signal monitored is the photobleaching of 2,5-diphenylfuran at 320 nm.

15. A method according to claim 1 wherein the HPLC is modified with a photochemical reactor which comprises:

(A) At least one pen shaped lamp which emits radiation in the range of about 190 nm to 800 nm;

(B) A cylindrical filter device wrapped around the lamp to selectively transmit a desired wavelength;

(C) A reaction chamber having a residence time of about 1 to 3 minutes crocheted from about 5 to 20 meters of thin polytetrafluoroethylene tubing having an internal diameter of about 0.1 to 2 mm and having a first open end and a second open end, the reactor being crocheted in the form of a cylinder with a diameter slightly larger than the combination of the lamp and the filter device and mounted snuggly therearound, and with the first open end of the polytetrafluoroethylene tubing connected to an analytical column of the HPLC and the second open end of the polytetrafluoroethylene tubing connected to the spectrophotometer of the HPLC; and (D) A piece of light reflective foil wrapped around the crocheted reaction chamber.

16. A method according to claim 15 wherein, in the photochemical reactor, two lamps which emit radiation in the range of about 190 nm to 800 nm are used.

17. A method according to claim 15 wherein the light reflective foil is aluminum foil.

18. A method according to claim 15 wherein the filter device is a cylindrical quartz sleeve of greater than 2 mm thickness.

19. A method according to claim 15 wherein, in the photochemical reactor, the filter device is a cylindrical quartz sleeve having a path length of about 4 mm containing a solution of 2,7-dimethyl-3,6-diazacyclo-hepta-2,6-diene at a concentration in the range of about 0.02 to 0.25 g/l.

20. A method according to claim 19 wherein the concentration of 2,7-dimethyl-3,6-diazacyclo-hepta-2,6-diene is about 0.042 g/l.

* * * * *